United States Patent [19]

Kubala et al.

[11] Patent Number: 5,614,417
[45] Date of Patent: Mar. 25, 1997

[54] SULFUR CHEMILUMINESCENCE DETECTION METHOD

[76] Inventors: Sidney W. Kubala, 220 Lasso St., Angleton, Tex. 77515; Donald N. Campbell, 2111 Twin Lakes Blvd., West Columbia, Tex. 77486; Robert D. Pearson, 2300 W. Alabama St., Apt. 68, Houston, Tex. 77098

[21] Appl. No.: 484,023

[22] Filed: Jun. 7, 1995

Related U.S. Application Data

[62] Division of Ser. No. 133,516, Oct. 7, 1993.

[51] Int. Cl.⁶ ............... G01N 33/00; G01N 21/76; G01N 21/72
[52] U.S. Cl. ............... 436/120; 436/119; 436/121; 436/155; 436/172; 422/52
[58] Field of Search ............... 436/119–121, 155, 436/172; 422/52

[56] References Cited

U.S. PATENT DOCUMENTS

| | | |
|---|---|---|
| 3,298,785 | 1/1967 | Reul . |
| 4,097,239 | 6/1978 | Patterson . |
| 4,190,368 | 2/1980 | Etess ............... 422/52 X |
| 4,352,779 | 10/1982 | Parks ............... 422/52 |
| 5,227,135 | 7/1993 | Godec et al. ............... 422/52 X |

FOREIGN PATENT DOCUMENTS

| | | |
|---|---|---|
| 2138997 | 10/1984 | United Kingdom . |
| 9420835 | 9/1994 | WIPO . |

OTHER PUBLICATIONS

R.M. Fristrom et al. *Combust. Flame* 1957, 1, 102–113.
P.L. Patterson et al. *Anal. Chem.* 1978, 50, 339–344.
P.K. Arora et al. *Can. J. Chem.* 1984, 62, 417–423.
J.S. Gaffney et al. *J. Chromatog.* 1985, 347, 121–127.
R.L. Benner et al. *Anal. Chem.* 1989, 61, 1268–1271.
H.–C. K. Chang et al, *J. Chromatog.* 1990, 517, 491–501.
H.–C. K. Chang et al. *Anal. Chem.* 1991, 63, 486–490.
A.L. Howard et al. *Anal. Chem.* 1993, 65, 724–729.
Farwell & Barinaga, Sulfur–Selective Detection with the FPD: *J. of Chroma. Sci*, Nov. 1986 pp. 483–494.

*Primary Examiner*—Arlen Soderquist
*Attorney, Agent, or Firm*—Chamberlain, Hrdlicka et al.; John Casperson

[57] ABSTRACT

This invention is directed to an improved total sulfur chemiluminescence detection system that uses a dual burner to generate the SO speckles for contact with ozone.

1 Claim, 6 Drawing Sheets

SULFUR CHEMILUMINESCENCE DETECTION METHOD

This is a divisional of copending application Ser. No. 08/133,516 filed on Oct. 7, 1993.

BACKGROUND OF THE INVENTION

1. Field of the Invention

This invention relates to photometric determinations of sulfur content of hydrocarbon compositions containing sulfur. More specifically, this invention is directed to chemiluminescence determinations and their utility in determining sulfur content.

2. Description of the Prior Art

R. L. Shearer, D. L. O'Neal, R. Rios, and M. D. Baker of Shell Development Company report in a paper entitled *Analysis of Sulfur Compounds by Capillary Column Gas Chromatography with Sulfur Chemiluminescence Detection*, published in *Journal of Chromatographic Science*, vol. 28, 24–28 (1990) that detection of sulfur content by means of sulfur chemiluminescence detection ("SCD") provides at least an order of magnitude improvement over flame photometric detection ("FPD") of sulfur. In fact, the article reports that an FID flame can be sampled directly into the reaction cell of an SCD system. The reaction cell stabilizes both the SO formed in the flame and reduces the interference of water and carbon dioxide by being run at low pressures. The amounts of SO produced will vary depending upon the air and hydrogen flow rates to the FID system burner. Upon the reaction of SO species with ozone a sulfur dioxide species forms that emits light in the wavelength region of 260 to 480 nanometers ("nm"). The optimal flow rates of hydrogen and air for FID and SCD are reported to be different.

R. L. Shearer reported in an article entitled, *Development of Flameless Sulfur Chemiluminescence Detection: Application to Gas Chromatography*, published in Analytical Chemistry, Vol. 64, No. 18, Sep. 15, 1992, pages 2192–6, the following problems: the SCD detector response was highly dependent on the condition and positioning of a ceramic probe that is used to sample the postflame gases from a flame ionization detector; and detector response could also be reduced when column bleed or other impurities accumulated on the probe (overcome by an inconvenient conditioning procedure). These problems were reportedly overcome by using an externally heated ceramic combustion assembly that is operated at low pressure and under fuel-rich conditions outside of the flammability limits of hydrogen and air. First a mixture of oxygen, make up and sample from a column are mixed and heated externally just prior to reaction in a combustion zone and then mixed with hydrogen in a space between a ceramic cylindrical core and outer walls. The resulting mixture is then sent through a transfer line to a chemiluminescence cell for reaction with ozone. The optimal thermal range reported was between 800°–900° C. The absolute signal increased with temperature, but so also did background noise. Air or oxygen could equally well be use, provided the stoichiometry of hydrogen and oxygen was the same.

Antek 6000 Process Nitrogen and Sulfur Analyzers, sold by Antek Industrial Instruments, Inc., Houston, Tex., is reported to be able to detect nitrogen and sulfur individually or simultaneously. Ultra-violet irradiation of the sample in a chamber and subsequent detection of the resulting fluorescence is used to determine the amount of sulfur present. Ozone is not used in any portion of the sulfur detection method.

Sievers Research, Inc., of Colorado, sells a Sievers Model 350 Sulfur Chemiluminescence System that utilizes SCD to determine the amount of sulfur present in a sample. The system uses a single stage hydrogen/air flame as the source for SO species.

R. L. Benner and D. H. Stedman report in an article entitled *Universal Sulfur Detection by Chemiluminescence* published in Ana. Chem. 1989, 61, 1268–1271, that both reduced and oxidized sulfur compounds could be measured simultaneously following sampling of a hydrogen flame into an ozone reactor at low pressures. Low pressure is required to ensure that no water vapor condenses, which condensation will interfere with ozone induced chemiluminescence. A drawing comparing a single flame system to a two stage system is shown in FIG. 2. Also disclosed are the criterion for hydrogen to oxygen ratios in the flame to maximize the signal to noise ratio. The fixed opening of a quartz sample tip that leads to the ozone reaction cell was varied as to distance from the hydrogen inlet to produce different residence times in the flame for a particular samples. R. L. Shearer reports in an article entitled, *Development of Flameless Sulfur Chemiluminescence Detection: Application to Gas Chromatography*, in Anal. Chem. 1992, 64, 2192–2196, that the SCD detector response is highly dependent on the condition and positioning of a ceramic probe that is used to sample the postflame gases from a flame ionization detector. This reference used a single stage pyrolysis process that preheated and combusted the gases prior to mixing with hydrogen at conditions that did not support a flame with the added hydrogen.

Although all reports concerning SCD indicate a substantial improvement over FPD, the following problems have been found in using SCD to measure sulfur content. When certain hydrocarbons are present in a sample being tested for sulfur content, there is an additional signal from some ozone induced reactions that do not involve sulfur, even though such hydrocarbons are first burned in a hydrogen/oxygen flame. Interestingly, hydrocarbons that contain oxygen are less likely to give rise to such signals. Some improvement in signal detection has been reported by N. Quickert et al. in an article entitled, *Modification of a Chemiluminescence Ozone Monitor for the Measurement of Gaseous Unsaturated Hydrocarbons*, published in *The Science of the Total Environment*, 3 (1975) 323–328 (Elsevier Scientific Publishing Company, Amsterdam, by selecting appropriate-light filters. However, even with such improvements interference from signals unrelated to sulfur content still occur. The sulfur chemistry in oxygen/hydrogen flames is believed to be very complicated (See article entitled *Sulfur-Selective Detection with the FPD: Current Enigmas, Practical Usage, and Future Directions*, by S. O. Farwell and C. J. Barinaga published in Journal of Chromatographic Science, Vol. 24, November 1986, pages 483–494). There are reported to be as many as thirteen equilibrium reactions, ten of which involve two interacting species, and three, involve three interacting species. Even ignoring the three reactions involving three species, the changes in sulfur distribution among the six possible sulfur containing species, i.e. HS, $H_2S$, SO, $SO_2$, S, and $S_2$, are expected to be determined by the kinetics of the overall bimolecular reaction scheme at each point in the flame; $S_2$ may not be a dominant species in such flames; variations in $H_2/O_2$ stoichiometry will also alter the sulfur distribution among the six species identified. J. C. Kramlich in his Ph.D. thesis from Washington State University, 1980, entitled, *The Fate and Behavior of fuel-sulfur in combustion*

*Systems*, reported that the concentration of sulfur in SO and SO$_2$ account for at least 85% of the total sulfur, whereas S$_2$ was predicted to never exceed a few pads-per-million. As had been observed and reported, the location of sampling the hydrogen/oxygen rich flame for transport into the ozone reaction cell has a significant impact on the strength of chemiluminescence observed. This is consistent-with the variation in sulfur distribution among the five species at each point in such flames.

This invention is in part based upon the discovery, that despite the complexity of the reactions occurring, the temperature and hydrogen/oxygen concentration dependence of the sulfur distribution among its various available species, as indicated above, results that are *consistent and reproducible can be obtained by using a dual flame system. Problems from variations in concentration changes among the various sulfur containing species unexpectedly do not occur. Interference from hydrocarbon diluents and carrier components give rise to far less signal interference, if any, observed when a dual flame system is used to burn the sulfur containing sample prior to introduction into an ozone reactor, as compared to that interference observed from a single stage flame system.

We have found that when using a single flame burner for the determination of total sulfur content (i.e. no separation of the sulfur components, just a direct injection of the entire sample into the flame) a significant positive interfering signal due to the hydrocarbon matrix was observed. Example 2 illustrates this problem.

SUMMARY OF THE INVENTION

General Statement of the Invention

Briefly, this invention resides in the use of a dual flame, or two stage flame system rather than a single stage system to generate a source of SO from sulfur containing samples. The system does not require a pyrolysis step in the hydrogen/oxygen combustion of a sulfur containing sample. Hydrocarbon interference from species commonly found in gasoline, and diesel fuels are significantly reduced over that which would otherwise be obtained from a pyrolysis method of combustion reported in the art. This invention makes a total sulfur determination possible without any significant preseparation of a sulfur containing sample into fractions. This type of separation may be done for example to lessen the hydrocarbon matrix of background materials present in a sample.

For purposes of this specification and claims, a plural stage burner system is one which has at least two flame controlling nozzles or tubes, wherein a flame from a first nozzle is introduced totally or substantially totally into a second nozzle along with additional flame supporting gases and then further burning, i.e. secondary burning is caused to occur immediately following the second burner. Such a plural burner is different from a pyrolysis burner system that does not involve two burners and smothers the flame downstream of the single stage burner by the addition of excess hydrogen. A single stage burner often will add hydrogen and a sample into the only nozzle or tube and then air or some other molecular oxygen containing gas about the orifice of the nozzle to initiate burning of both the sample and hydrogen carrier gas. By contrast, in a plural stage system, a lower combustion supporting gas stream comprising combustion supporting gases like hydrogen, and low molecular weight hydrocarbons, such as methane, acetylene, and propane, or oxygen and preferably with a sulfur containing sample to be analyzed is introduced into a first or lower burner and ignited with a stream of, for example, a combustion supporting gas comprising hydrogen, low molecular weight hydrocarbons, such as propane, acetylene, methane, and the like, or molecular oxygen containing gas is introduced just downstream of the exit orifice of the lower burner. Substantially all of the hydrogen or molecular oxygen containing gas introduce and the flame produced therewith by the lower burner are introduced into an upper burner. Downstream of the upper burner an additional stream of preferably air or other molecular oxygen containing gas is introduced that continues the burning of at least some of the hydrogen which was added downstream of the lower burner orifice and any unreacted or partially reacted hydrocarbon species present in the sample introduced into the lower burner with the lower gas stream, which may contain air or hydrogen, but is preferably air. For purposes of this Specification and claims, combustion supporting gas can include inert or non-reactive components, such as nitrogen, argon, helium, and the like. To be combustion supporting all that is necessary is that those components present in the presence of molecular oxygen will burn with enough heat to reach temperatures in excess of about 800° C., preferably in excess of about 900° C. and still more preferably in excess of about 1000° C.

in summary the advantages made available by this invention include: specificity to sulfur, equal molar responses to various sulfur compounds, little if any hydrocarbon or carbon dioxide quenching, a linearity over a wide dynamic range of concentrations, and sufficient reliability to satisfy current regulatory requirements for the determination of sulfur content.

Dual flame systems useful in this invention are commonly referred to in the art to be dual-flame burners. An example of one such system that is commercially available from Varian for use in flame photometric detection systems.

In Order to maximize the benefits from using a two stage flame, we have discovered in the case of C$_7$ (like heptane) and C$_{16}$ hydrocarbons that the amount of hydrogen was not critical, since a broad range in amounts could be used without significant impact on results. Oxygen components were preferably in excess over the carbon content. Since results were linear in sulfur, the excess of hydrogen over sulfur did not change the results appreciably. The excess preferably is 220–400 fold on a molar basis, more preferably, it is 250–370 fold, and most preferable, it is 280–340 fold. We have further-discovered that the ratios of hydrogen to air in the case of a single stage flame is not significantly different from that ration appropriate to the second stage of a two stage flame. The relative location of the quartz orifice leading to the reaction cell containing ozone was the same in the dual stage flame system as compared to that for the single stage flame.

Surprisingly, the impact that varying the distance between a single stage burner and the quartz inlet to an ozone reactor under reduced pressure in a typical SCD System did not preclude making significant improvements in performance when a dual flame system was substituted for that of a single stage flame system. Among the improvements that were achieved as a result of a two stage flame is: a significant decrease in hydrocarbon interference, which in part will depend upon the nature of the hydrocarbon, e.g. aromatic versus aliphatic (saturated or unsaturated) etc. This was clearly demonstrated in the case of heptane with and without sulfur-containing species. Coking problems that sometimes arose in the case of a single stage flame were substantially lessened, and often eliminated in the case of a dual flame system.

Utility and Objects of the Invention

This invention provides operating advantages over a single stage flame system in determining sulfur content by chemiluminescence. It is an object of this invention to achieve a significant portion of such operating efficiencies by substituting a dual flame system in place of a single stage flame system within the context of an SCD system. For example when using the dual-flame system for the analysis of sulfur in benzene, the enhanced combustion realized with the dual-flame system significantly reduced the positive interfering signal noted in the single-flame system. Example 2 illustrates this point. Using a similar hydrogen/air ratio in the second flame of the dual burner system when compared to the single flame system, injections of benzene (no added sulfur) gave virtually no response (see "A"). When 106 ppm sulfur is added to the benzene, a large signal is observed (see "B"). The examples of items 3 and 6 also point out that an enhancement in sensitivity (approximately a factor of 2 in this case when using peak heights) is realized in the dual-flame system over that of a single flame.

DETAILED DESCRIPTION OF THE DRAWINGS AND PREFERRED EMBODIMENT

Figure 1:
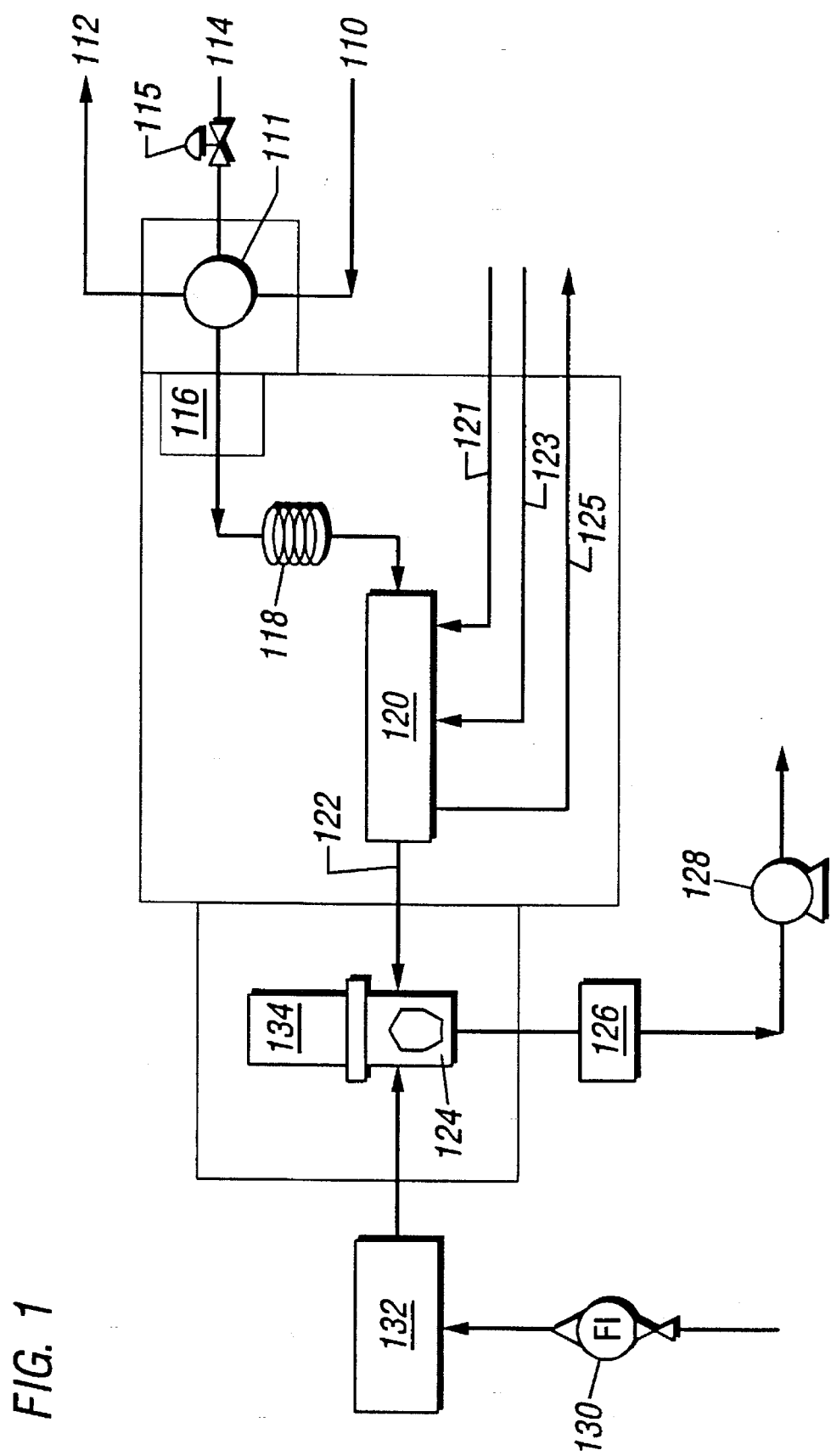
FIG. 1 is a schematic overview of an SCD system, disclosing the stages of sample preparation, and transfer from initial injection into a flame to introduction into a chemiluminescence reaction cell for contact with ozone.
Figure 2A:
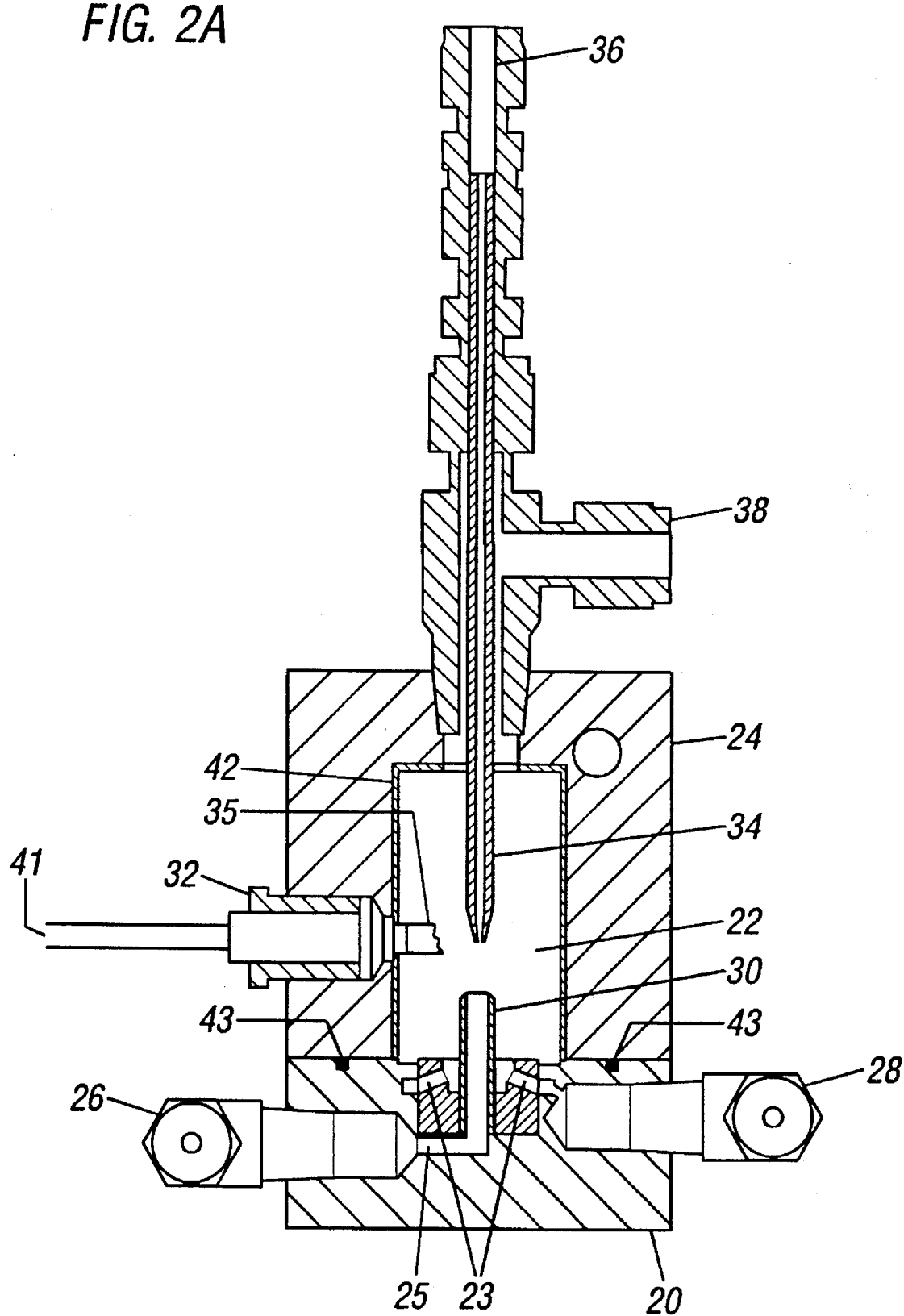
FIG. 2 shows a side by side comparison of the differences between a single versus a dual stage burner.
Figure 2B:
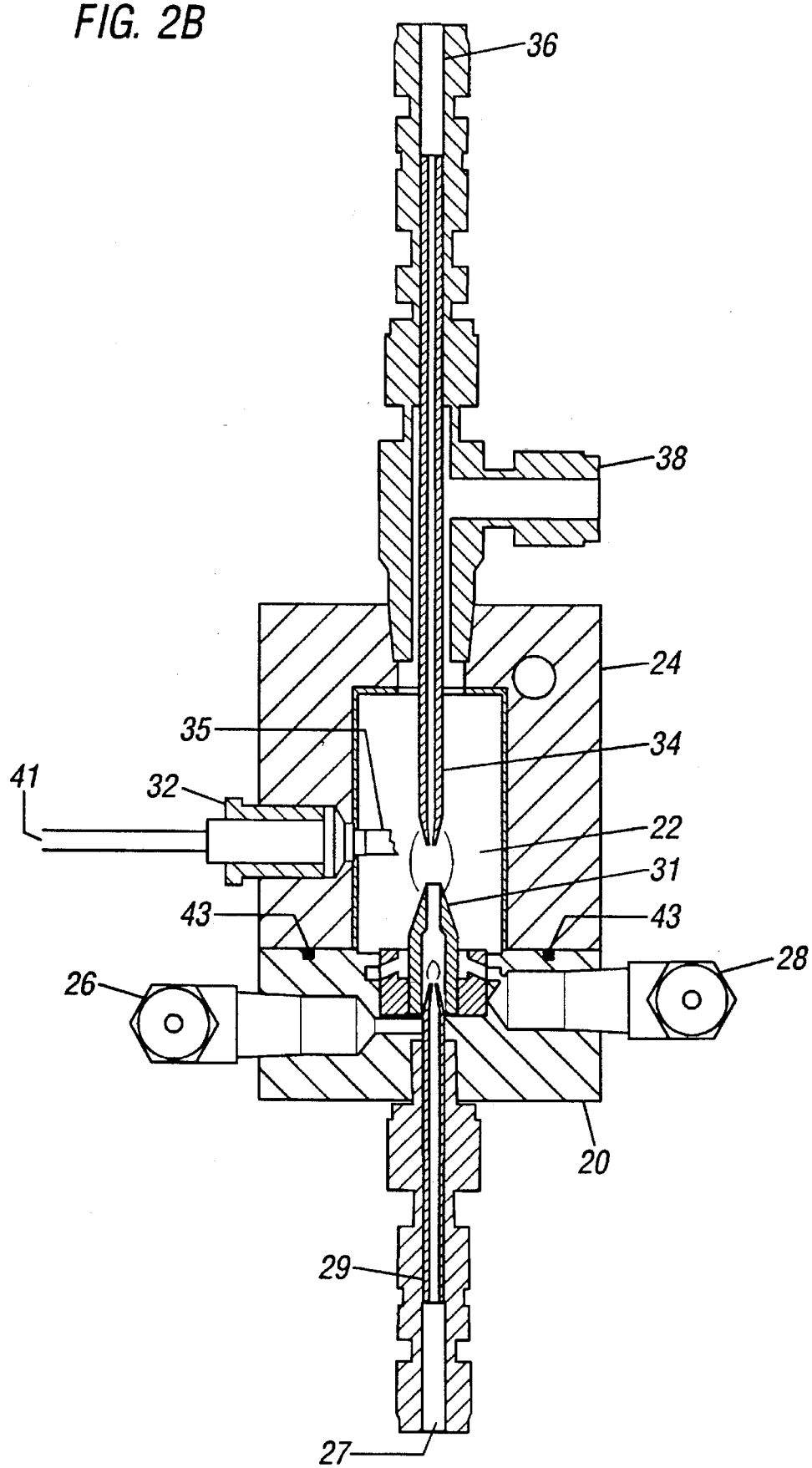

Referring to FIG. 1, the working elements of a typical SCD, Sulfur Chemiluminescence Detector System, are: a means for introducing a fixed amount of sample into a carrier gas, which means corresponds to: sample inlet 110, injection valve assembly 111, carrier gas inlet 114, carrier regulator 115, wherein any excess is removed through a sample outlet valve 112 which arrangement permits on line monitoring of a sample stream from some source not shown; a means 116 for conditioning a sample stream by flashing to completely volatize that portion of any sample introduced through said sample inlet 110 which is to be transferred into a substantially inert column 118, a means 120 for burning the sample, such as a single stage burner 2a shown in FIG. 2, that can have hydrogen, and air inlets shown respectively, in FIG. 1 as lines 121, and 123 with an atmospheric vent line 125; a means 122, such as a sample tube 34 of FIG. 2, for transferring at least a portion of such burned sample that exits burner 120, into reaction chamber 124, such as fitting 36 shown in FIG. 2 that connects the sample tube 34 to a transfer line that connects to chemiluminescence cell 124 along with a trap 126; vacuum pump 128; and a source of ozone for the reaction chamber 124, comprising for example an air supply from a source not shown, measuring valve 130 for the air supply not shown, and an ozone generator 132; and finally a detector 134 to measure the chemiluminescence that results from mixing ozone with transferred material from burner 120. Optionally, but preferably there can be a filter for desired wavelengths between reaction chamber 124 and detector 134.

Referring to FIG. 2, the working parts of a single versus a dual stage burner are shown. Many of the same elements are present in each, along with certain very important differences. In the single stage burner system (shown as 2a in FIG. 2), there are: a gas inlet block 20, a flame box 22, determined by a fire block 24, hydrogen inlet assembly 26, air inlet assembly 28, burner 30, electrically activated ignitor 32, sampling tube 34, a schematic arrangement of a fitting 36 shown in FIG. 2 that connects the sample tube 34 to a transfer line that connects to chemiluminescence cell 124 and an atmospheric vent 38. The working pads of a dual stage burner system (shown as 2b in FIG. 2) consist of: a gas inlet block 20, a lower burner 29, an upper burner 31, a hydrogen gas inlet assembly 26, an upper air inlet assembly 28, a lower air and sample carrier assembly inlet 27 connected to a source not shown, an electrically activated ignitor 32, a sampling tube 34, fitting 36 shown in FIG. 2 connects the sample tube 34 to a transfer line that connects to an atmospheric vent 38.

For purposes of understanding FIGS. 3 and 4, briefly the operation of each of the burner systems of FIG. 2 is discussed in the immediately following paragraphs.

In a single burner system, such as 2a shown in FIG. 2, a sample of the material to be analyzed for sulfur content is carried along by hydrogen and a sample carrier gas or solution through a valve (not shown) into a hydrogen inlet system 26, through a hydrogen pathway 25 directly into burner 30. Air or oxygen containing gas is introduced through air assembly 28 through pathways 23 that surround the outside surface of burner 30. The amount of flow of all gases can be very accurately controlled in cc's/min. As the hydrogen and sample emerge from burner 30 and mix with molecular oxygen or some other oxidizing gas, the mixture is ignited by filament 35, which is an electrically heated wire extending into fire box 22 from ignitor assembly 32. The filament 35 is kept at the ignition temperature necessary to cause burning of the mixture of gases within flame box 22 by means of energy provided from a power source not shown through wires 41, in the event of a flame-out. In the more usual case, the flame is self-sustaining. The amount of voltage, if any, applied to wires 41 is determined by a temperature probe not shown which maintains filament 35 at some desired temperature. Usually, once a flame has been initiated, the flame issuing from: burner 30 will keep filament 35 sufficiently hot and also maintain the flame. However, sensors not shown, which monitor the temperature of filament 35, maintain filament 35 at least at such flame initiation temperature by passing a current of electricity through filament 35 from wires 41 until such temperature is reached and maintained. Upper block 24 defines a flame or fire box 22 and is sealed to lower block 20 with an O-ring or other seal 43. Along the inner surfaces 42 within flame box 22 is preferably a protective coating such as teflon to reduce wear of such inner surfaces due to attack by sulfur and other flame gases. Ignited gases within flame box 22 are vented in part through an atmospheric vent 38 with the remainder entering sampling tube 34 for transmission to chemiluminescence cell via fitting 36. The transfer to cell via fitting 36 is preferably caused by means of a low pressure pump (not shown) which is downstream of the chemiluminescence cell 124 shown in FIG. 1. The relative amounts of flame products entering cell 124 are roughly 30–50% of all gasses issuing from burner 30 and air assembly 28 and 50–70% of them exit the system through atmospheric vent 38. The relative flows of all material entering the system are controlled, for instance, in the case of hydrogen flow rates in the range 80–160 cubic centimeters/minute ("cc/min.") within a variance of ±2%; air flow rates in the range 150–300 cc/min. within a variance of ±2%. The total hydrogen relative to air or oxygen is not critical, provided an ultimately reducing atmosphere is maintained in the flame box, i.e. an excess of hydrogen over oxidizing species. The location of sampling tube 34 relative to the opening of burner 30 is on the order of approximately 4 millimeters ("mm") and is adjustable. A window not shown is preferably present through one wall of fire box 22 to permit visual alignment of sampling tube 34. Generally, the intensity of chemiluminescence found decreases with an increasing gap between outlet of burner 30 and inlet of sampling tube 34. The observed intensity similarly falls off with horizontal misalignment of burner opening relative to that opening of sampling tube 34.

Referring to dual burner system 2b of FIG. 2, the operation is as follows. Lower air and sample carrier enter lower gas assembly 27 through a valved pathway not shown into lower burner 29. Exiting lower burner 29 are gases which directly flow into upper burner 31 along with a hydrogen gas stream. The hydrogen gas stream enters through hydrogen gas assembly 26. Within hydrogen gas assembly is a valved passageway. The amount of hydrogen introduced into upper burner 31 around outlet of lower burner 29 is very accurately controlled by a regulator not shown. The manner of introduction is such as to cause the hydrogen introduced around outlet of lower burner 29 to mix with a stream of lower air and sample carrier while passing through upper burner 31. Preferably substantially all of the material leaving from lower burner 29 and that entering through hydrogen inlet assembly 26 mix thoroughly during passage through upper burner 31. Upon exiting upper burner 31, ignitor 32 causes gases leaving upper tube or burner 31 to ignite initially, but usually the flame will be self-sustaining thereafter. In addition to igniting those gases which exit upper burner 31, the orifice sizing of and flow rate through upper burner 31 is such that there will occur a flame propagation back through upper burner 31 and the gases flowing therethrough so as to ignite gases exiting lower burner 29. Back flame propagation is designed to cease at the orifice of lower burner 29. Once flame propagation has occurred, the burners are designed to maintain uniform burning without the need for continuous or continual back burning ignition or even filament ignition of upper burner 31 by ignitor 32. The details necessary to achieve this type of burning is well known from the application of dual burners in flame photometric detection systems.

An example of the relative rates of flow of gases introduced into the dual burner when in typical operation for sulfur chemiluminescence of this invention is as follows: the hydrogen flow rate is at 170–240 cc/min. with a variance of no more than ±2%, upper air, at 110–200 cc/min. with a variance of no more than ±2%, and lower air, at 60–120 cc/min. with a variance of no more than ±2%. The combustion products are transferred into the ozone reaction cell at a sufficiently low pressure, such as a pressure in the range of 28–29.5 inches of mercury, to stabilize any SO that was formed by the combustion means and prevent condensation of water or other interfering species.

In summary, the essential difference between a Single stage and dual stage flame system resides in the presence of more than one flame controlling burner or nozzle with the separate and independent introduction of secondary flame sustaining gases into each nozzle or burner coupled with the ability of each secondary nozzle, e.g. an at least one upper nozzle capable of propagating a flame by back ignition to its immediately lower burner. Surprisingly, in the case of SCD, the species produced upon introduction into an ozone reaction cell do not give rise to as significant a level of interfering signals that would otherwise mask the signal arising from the presence of sulfur in the form of sulfur monoxide radicals. The use of a dual flame system as defined above has been used for FPD, flame photometric detection, wherein the emission spectrum of highly activated chemical species is caused by air or molecular oxygen initiated oxidation in contrast to ozone reaction with sulfur monoxide leading to sulfur chemiluminescence.

Detailed Description of the Invention and Preferred Embodiments

EXAMPLE 1

Example 1 discloses the optimum conditions for dual and single stage flame sulfur chemiluminescence determinations, to contrast the differences in concentrations, flow rates, and any other relevant operating parameters which impact operation. The difference in operation are clearly show by comparing the graphs of FIG. 3 with those of FIG. 4. There is always an excess of hydrogen over oxidative components in the flame which is introduced into sampling tube 34. Sample tube 34 is preferably made of a material that is inert to and otherwise unaffected by the temperature and components of the flame which is in part introduced into it. Flow rate of hydrogen and air are each controlled to ±0.2 pounds, at a flow rate controlled to ±2% cc/min.

Figure 3A:
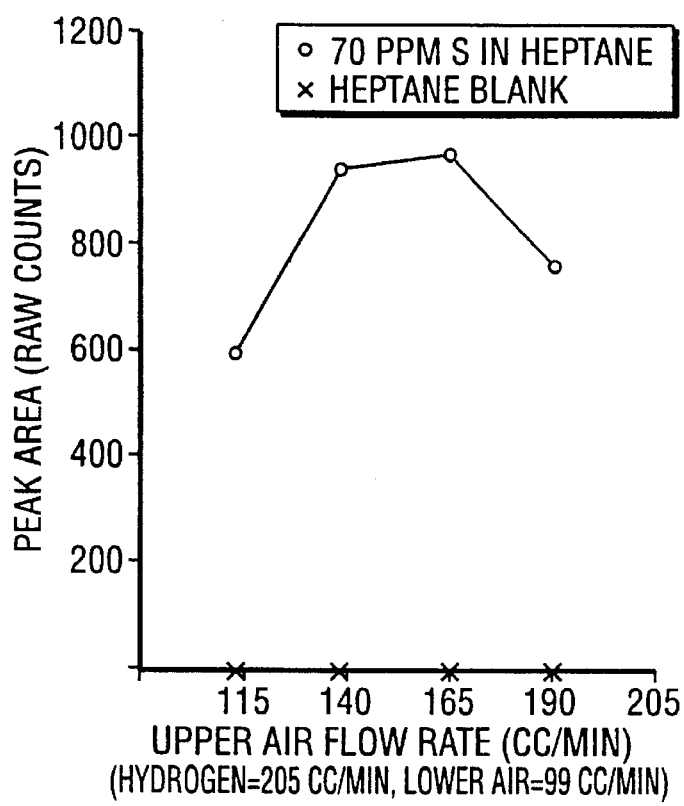
FIG. 3A is a graph of Intensity in some arbitrary units that depend upon optimizing the instrument and setting the time scale for integrating intensity over time (usually 10–20 seconds, the anticipated time to elute a sample from a selected column) as a function of upper air flow rate.
Figure 3B:
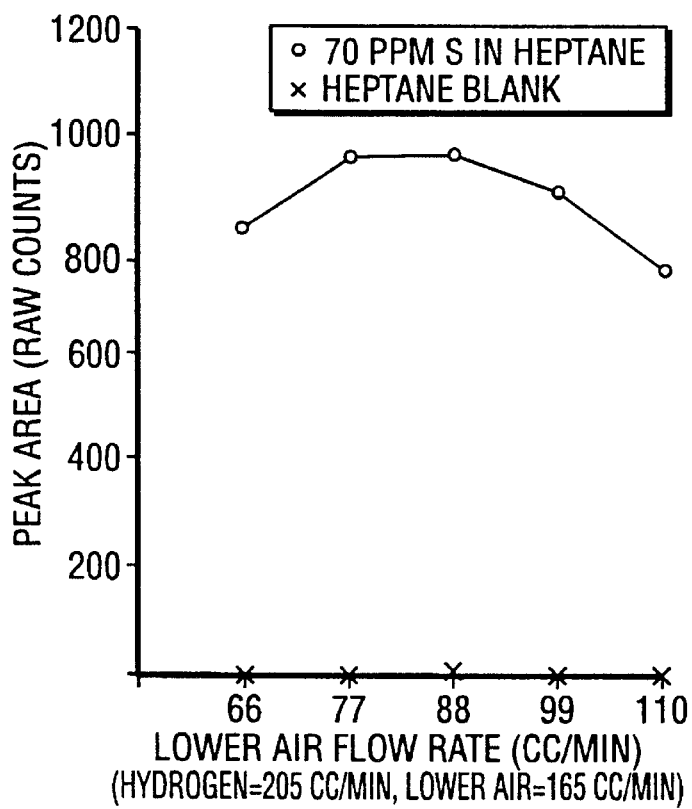
FIG. 3B is a graph of intensity (as defined above) as a function of lower, burner air flow rate in cubic centimeters per minute (cc/min.)
Figure 3C:
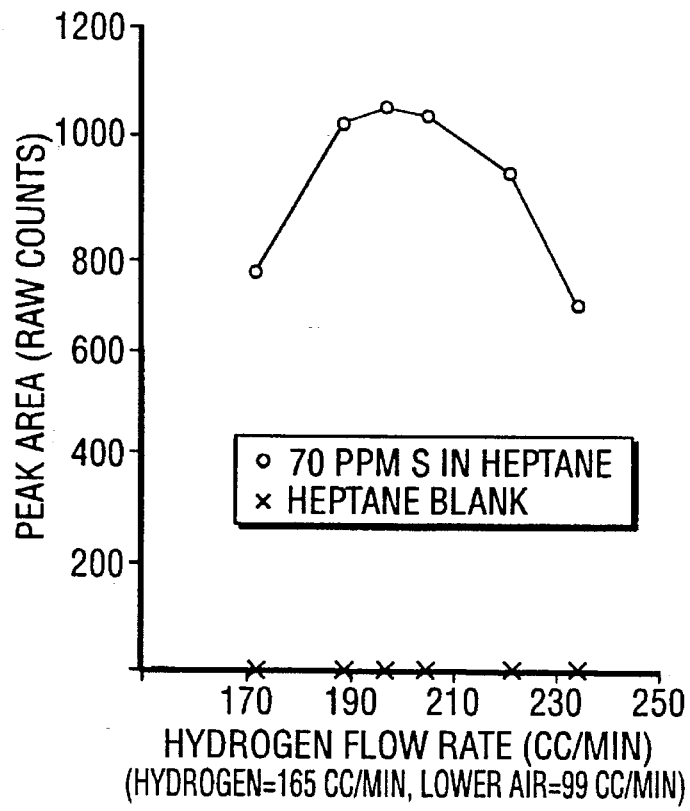
FIG. 3C is a graph of Intensity (as defined above) as a function of hydrogen flow rate in cc/min.
Figure 4A:
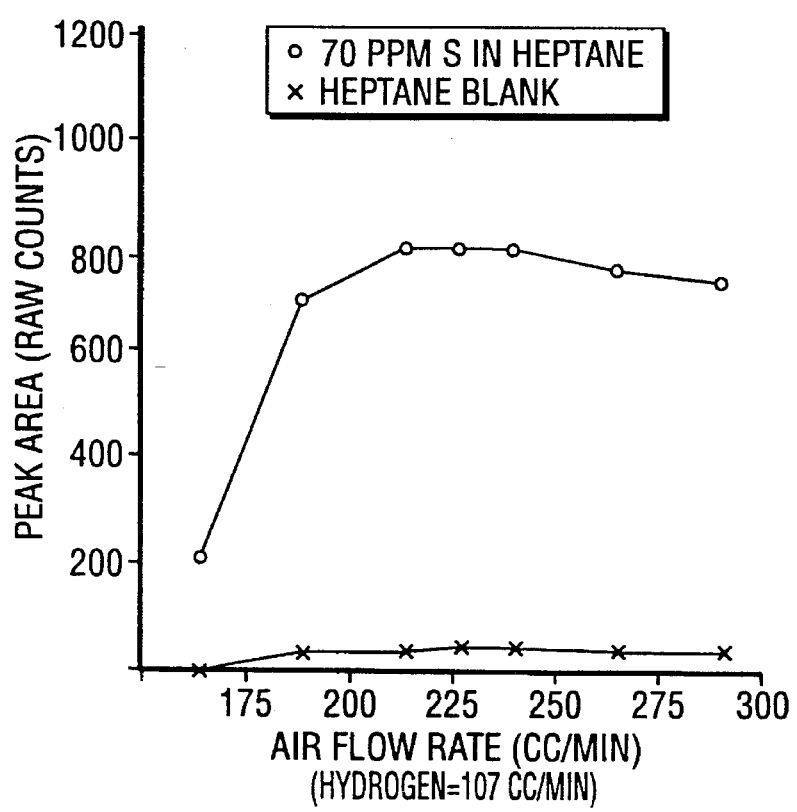
FIGS. 4A and 4B, are graphs, each of which corresponds, respectively, to FIGS. 3A, and 3B, for a single stage rather than a two stage burner.
Figure 4B:
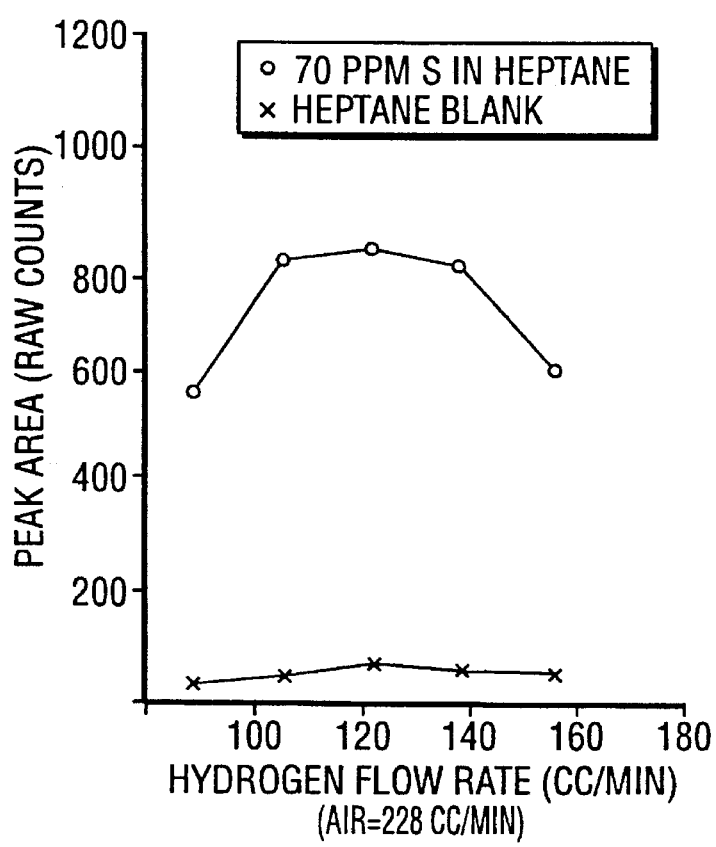

FIGS. 3A, 3B, and 3C graphically illustrate the effect of varying the upper air, lower air, and hydrogen flow rates in the dual burner system, respectively. FIGS. 4A and 4B graphically illustrate the effect of varying the air and hydrogen flow rates in the single burner system, respectively. Using a 0.1 microliter sample volume, samples consisting of heptane (a $C_7$ hydrocarbon) with approximately 70 parts per million (ppm) and without added sulfur (blank) were injected into the two different burner systems under identical instrumental conditions (injection temperature, probe height, etc.). Peaks were recorded for the two samples while varying the above mentioned flows and compared in FIGS. 3 and 4. The figures demonstrate an increase in sensitivity, as well as demonstrating the decrease in interference due to the hydrocarbon matrix.

The settings which gave rise to the results plotted in FIGS. 3 and FIGS. 4 are set out in the following table:

| Dual Stage Burner Sample Tube Flame Temperature: ≧800° C. | Hydrogen Flow Rate | Upper Air Flow Rate | Lower Air Flow Rate | Distance of Sampling Tube from Flame |
|---|---|---|---|---|
| FIG. 3A | 205 cc/min. | 114–190 cc/min. | 99 cc/min. | 4 mm |
| FIG. 3B | " | 165 cc/min. | 66–110 cc/min. | " |
| FIG. 3C | 170–240 cc/min. | 165 cc/min. | 93 cc/min. | " |
| Single Stage Burner Sample Tube Flame Temperature: ≧800° C. | Hydrogen Flow Rate | Upper Air Flow Rate | Lower Air Flow Rate | Distance of Sampling Tube from Flame |
| FIG. 4A | 107 cc/min. | 160–300 cc/min. | NR | 4 mm |
| FIG. 4B | 90–160 cc/min. | 228 cc/min. | NR | " |

Note the temperature of all gases on introduction are at 100° C.

EXAMPLE 2

Example 2 is a comparative example of the dual versus single stage flame operation in the context of an SCD system.

Figure 5A:
FIG. 5 graphically illustrates the peak profiles obtained for both the heptane blank (A) and the added sulfur in heptane sample (B) with a single stage burner system and the dual stage burner system.
Figure 5B:
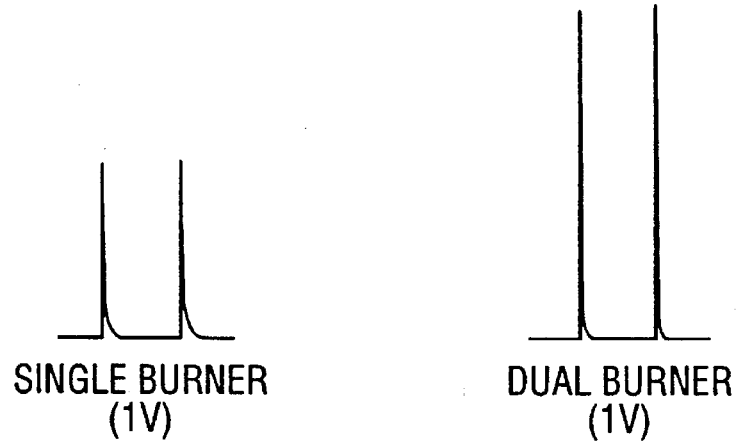

FIG. 5 graphically illustrates the peak profiles obtained for both the heptane blank (A) and the added sulfur in heptane sample (approximately 70 ppm sulfur) (B) with the two burner systems, one a dual stage combustion system and the other a single stage combustion system.

FIG. 5 demonstrates the increase in sensitivity when using the dual burner system when compared to the single burner system (approximately a factor of two when using peak height). In addition, the interference noted in the single burner system due to the hydrocarbon matrix is substantially lessened when using the dual burner system.

Modifications

Specific compositions, methods, or embodiments discussed in this Specification are intended to be only illustrative of the claimed invention. Variations of any of these that would be readily apparent to a person of skill in the at based upon the teachings of this Specification and skills of a person of ordinary skill in the relevant art are intended to be within the scope of the disclosed invention.

Reference to documents made anywhere in the Specification is intended to result in such documents, be they patents, or any other printed publication, including documents referenced in such documents, are intended to be expressly incorporated herein by reference in their entirety.

Each expressly identified numerical range within this Specification is intended to incorporate by reference and therefore expressly include and provide express support as required by 35 U.S.C. 112 for each and every numerical member of each such range including each and every possible range within each such expressly identified numerical range. For example, a numerical range of 1 to 100, is intended to provide express support for any range within such numerical range, such as 3 to 28, or 72 to 94 etc. and also to provide express support for any specific numerical member of the range 1 to 100, such as 25, or 63 etc.

We claim:

1. A process comprising forming a mixture of sulfur-containing gas and oxidizing gas;

partially combusting said mixture in the presence of added hydrogen in a first stage to form first stage combustion gases;

conveying said first stage combustion gases to a second stage combustion zone;

introducing additional oxidizing gases into said second stage combustion zone;

further combusting said first stage combustion gases in said second stage combustion zone to form second stage combustion gases containing SO;

conveying at least a portion of said second stage combustion gases to an ozone reaction chamber;

introducing ozone into said ozone reaction chamber to react with the SO and form a chemiluminescent reaction product; and measuring the chemiluminescence given off by the reaction product;

wherein the temperature in the second stage combustion zone is ≧800° C.; and wherein the pressure in the ozone reaction chamber is in the range of 28–29.5 inches of mercury.

* * * * *